United States Patent
McKellar

(10) Patent No.: US 7,229,084 B2
(45) Date of Patent: Jun. 12, 2007

(54) CHAIR CONVERSION DEVICE

(75) Inventor: Douglas Scott McKellar, Oakville (CA)

(73) Assignee: J. Sterling Industries Ltd., Woodbridge, Ontario (CA)

( * ) Notice: Subject to any disclaimer, the term of this patent is extended or adjusted under 35 U.S.C. 154(b) by 326 days.

(21) Appl. No.: 10/770,354

(22) Filed: Feb. 2, 2004

(65) Prior Publication Data

US 2004/0207244 A1   Oct. 21, 2004

Related U.S. Application Data

(60) Provisional application No. 60/461,442, filed on Apr. 9, 2003.

(51) Int. Cl.
   *B62B 1/00* (2006.01)
(52) U.S. Cl. ............... 280/79.2; 280/47.25; 280/47.33
(58) Field of Classification Search ............ 280/47.34, 280/47.371, 47.19, 47.26, 87.021, 643, 304.1, 280/79.2, 47.25, 47.33; 297/188.2, 188.6, 297/DIG. 4, 440.2; 248/125.8, 129; 224/275, 224/407, 570

See application file for complete search history.

(56) References Cited

U.S. PATENT DOCUMENTS

| | | | | | |
|---|---|---|---|---|---|
| 3,338,628 | A | * | 8/1967 | Evans | 297/188.2 |
| 3,704,025 | A | * | 11/1972 | Cerveny et al. | 280/643 |
| 4,045,044 | A | * | 8/1977 | Bierer | 280/87.021 |
| 4,266,765 | A | * | 5/1981 | Sandoval et al. | 280/47.371 |
| 4,431,206 | A | * | 2/1984 | Pryor | 280/304.1 |
| 4,506,903 | A | * | 3/1985 | Bowermaster | 280/304.1 |
| 4,696,420 | A | * | 9/1987 | Kulik | 224/275 |
| 4,905,944 | A | * | 3/1990 | Jost et al. | 248/125.8 |
| 5,340,140 | A | * | 8/1994 | Bynum | 280/304.1 |
| 5,344,169 | A | * | 9/1994 | Pryor et al. | 280/79.3 |
| 5,882,083 | A | * | 3/1999 | Robinson | 297/440.2 |
| 6,105,980 | A | * | 8/2000 | Cino et al. | 280/79.2 |
| D434,502 | S | * | 11/2000 | Gallant | D24/185 |
| 6,273,444 | B1 | * | 8/2001 | Power | 280/304.1 |
| 6,325,097 | B1 | * | 12/2001 | Gallant et al. | 137/505 |

* cited by examiner

*Primary Examiner*—Hau Phan
(74) *Attorney, Agent, or Firm*—Rankin, Hill, Porter & Clark LLP

(57) ABSTRACT

Disclosed herein is a device for equipping a recliner with one or more accessories, comprising a base frame portion attachable to the recliner, the base frame having a plurality of mounting locations and a plurality of recliner accessories, each of which is arranged for removable attachment to a corresponding one or more of said mounting locations.

20 Claims, 10 Drawing Sheets

CHAIR CONVERSION DEVICE

REFERENCE TO CO-PENDING APPLICATIONS

The entire subject matter of U.S. Provisional application Ser. No. 60/461,442 filed Apr. 9, 2003 and entitled RECLINER ACCESSORY DEVICE is incorporated by reference. The applicant claims priority benefit under Title 35, United States Code, and Section 119(e) of U.S. Provisional application Ser. No. 60/461,442 filed Apr. 9, 2003 and entitled RECLINER ACCESSORY DEVICE.

BACKGROUND OF THE INVENTION

1. Field of the Invention

The present invention relates to chairs and more particularly, but not necessarily exclusively to mobile or stationary recliner chairs for medical patients.

2. Description of the Related Art

In recent years, there has been an increase in the level of comfort available to people in their residences, in large part by the ubiquitous recliner known by the trade name LA-Z-BOY. Recliners of this brand and others similar to it come in an increasingly wide array of colours, fabrics, styles, all with the intent of providing reclining comfort to the owner.

However, there has been relatively fewer recliner products available in medical environments such as hospitals and nursing homes and those that are available are usually of limited comfort and bland in appearance.

It is an object of the present invention to provide a novel chair and method of equipping a chair for medical and other environments.

SUMMARY OF THE INVENTION

In one of its aspects, the present invention provides a device for equipping a recliner with one or more accessories, comprising a base frame portion attachable to the recliner, the base frame having a plurality of mounting locations and a plurality of recliner accessories, each of which is arranged for removable attachment to a corresponding one or more of said mounting locations.

In an embodiment, the base frame includes a pair of first plates positioned for engaging opposite side regions of the recliner, a pair of second plates positioned for engaging a back wall region of the recliner, and at least one third plate for engaging a bottom region of the recliner.

In an embodiment, one or more accessories are medical accessories.

In an embodiment, a number of the mounting locations are positioned on one or more of the first plates, one or more of the second plates, or both. One or more of the locations includes a means for engaging an elongate member on one or more of the accessories.

In an embodiment, one or more of the engaging means includes a sleeve portion dimensioned to receive the elongate member therein.

In an embodiment, one or more of the sleeve portions are located on the first, second or third plates.

In an embodiment, the accessories include one or more IV poles, one or more medication containers, one or more tray rods and trays, two push handles for recliners with wheels, one or more urinary hooks or a combination thereof.

In an embodiment, the second plates are spaced from one another, wherein one of the engaging means is operable to carry a medication container.

In an embodiment, the engaging means includes at least one clamp member which is dimensioned to clamp an outer surface of the medication container.

In an embodiment, the accessories include one or more push bars.

In an embodiment, one of the accessories is a tray. The tray includes a support arm and one of the mounting locations includes a support arm receiving formation. The support arm receiving formation includes a sleeve portion.

In another of its aspects, there is provided a recliner chair device, comprising a recliner frame supporting a seat portion, a back portion and a pair of arm portions, an accessory portion attachable to the recliner frame for equipping the recliner chair device with one or more accessories, the accessory portion including an accessory base frame portion attachable to the recliner frame, the accessory base frame having a plurality of mounting locations and a plurality of recliner accessories, each of which is arranged for removable attachment to a corresponding one or more of said mounting locations.

In one of its aspects, the present invention provides a device for equipping a recliner with one or more accessories, comprising a base frame means having a periphery which is complementary with and removably attachable to a section of the recliner, the base frame means a number of mounting means, and a plurality of recliner accessories, each of which is arranged for attachment with a corresponding one or more of said mounting means, in order to be positioned in an operative position on an exterior of the recliner.

In one of its aspects, the present invention provides a device for equipping a recliner with one or more accessories, comprising a base frame portion having a periphery which is complementary with and removably attachable to a section of the recliner, the base frame including a number of mounting locations, and a plurality of recliner accessories, each of which is arranged for attachment to a corresponding one or more of said mounting locations, in order to be positioned in an operative position on an exterior of the recliner.

In an embodiment, a first sleeve member is provided at one or more of the mounting locations. The first sleeve member is positioned so as to be exposed to or accessible from a peripheral region of the recliner. In one example a pair of first sleeve members are provided at one or more of said mounting locations. The pair of first sleeve members is arranged to be oriented horizontally adjacent a side peripheral edge region, a rear peripheral edge region or a front peripheral region of the recliner.

In an embodiment, a second sleeve member is provided at one or more of the mounting locations. The second sleeve member is arranged to be oriented vertically adjacent a side peripheral edge region, a rear peripheral edge region or a front peripheral edge region and to be exposed to or accessible from a peripheral region of the recliner. In one example, each of the second sleeve members is be arranged to be oriented vertically and positioned adjacent a side face, a rear face or a front face of the recliner and one or more of the second sleeve members is arranged to be oriented vertically and positioned near a respective corner of the recliner.

In an embodiment, the device further comprises an undercarriage to render the recliner mobile when the device is mounted thereon. The undercarriage preferably includes a pair of rear caster wheels, each of which is mounted on the base frame portion in order to be located against each rear corner of the recliner when the device is mounted thereon. If desired, the undercarriage includes a pair of front caster wheels, each to be located against each front corner of the recliner when the device is mounted thereon. If desired, the front caster wheels may include a caster wheel frame member which is separate from the base frame portion.

In an embodiment, the base frame portion includes a pair of corner formations, each to enclose a corresponding corner region of the recliner when the device is mounted thereon. In this case, a frame member is provided for joining the corner formations together. Each corner formation may include one or more of a bottom portion to engage a bottom region of the recliner, a side portion to engage a side region of the recliner and a rear portion to engage a rear region of the recliner. In this case, the bottom, side and rear portions respectively include a bottom, side and rear panels which are attached together at adjacent edges thereof. The frame member may be length adjustable to adjust the spacing between the corner formations, thereby to accommodate recliners of varying dimensions and the first and second sleeve members may be in orientations other than horizontal and vertical In one embodiment, the accessories include one or more push bars positionable in selected ones of the second sleeve members for pushing the recliner, one or more trays, document holders, or carriers for securing and/or positioning articles on the recliner.

In another of its aspects, the present invention provides a mounting bracket for equipping a recliner with one or more recliner accessories, comprising a base frame portion having a periphery which is complementary with and removably attachable to a rear section of the recliner, the base frame including a number of mounting locations for receiving the accessories in an operative position on an exterior of the recliner.

In still another of its aspects, the present invention provides a recliner comprising a recliner frame supporting a seat portion, a back portion and a pair of arm portions, a mounting bracket mounted on the recliner and a number of recliner accessories removably attached to the mounting bracket, the mounting bracket further comprising a base frame portion having a periphery which is complementary with and removably attachable to a section of the recliner, the base frame including a number of mounting locations, each of the recliner accessories arranged for attachment to a corresponding one or more of said mounting locations, in order to be positioned in an operative on an exterior of the recliner.

In still another of its aspects, the present invention provides a method of equipping a recliner with accessories, comprising the steps of:
providing a recliner with a frame supporting a seat portion, a back portion and a pair of arm portions;
providing a mounting bracket assembly with a base frame portion having a periphery which is complementary with and removably attachable to a rear section of the recliner;
providing a number of mounting locations on the mounting bracket assembly for removably mounting a number of recliner accessories thereon;
installing the mounting bracket assembly on the recliner; and
installing the accessories on the mounting bracket.

In still another of its aspects, the present invention provides a method of equipping a recliner with accessories, comprising:
a step for providing a recliner with a frame supporting a seat portion, a back portion and a pair of arm portions;
a step for providing a mounting bracket assembly with a base frame portion having a periphery which is complementary with and removably attachable to a rear section of the recliner;
a step for providing a number of mounting locations on the mounting bracket assembly for removably mounting a number of recliner accessories thereon;
a step for installing the mounting bracket assembly on the recliner; and
a step for installing the accessories on the mounting bracket.

In still another of its aspects, the present invention provides a mounting bracket for equipping a chair with one or more accessories, comprising a base frame portion having a periphery which is complementary with and removably attachable to a section of the chair, the base frame including a plurality of mounting locations for receiving the accessories in an operative position on an exterior of the chair.

In still another of its aspects, the present invention provides a chair comprising a chair frame supporting a seat portion and a back portion, a mounting bracket mounted on the chair and a number of chair accessories removably attached to the mounting bracket, the mounting bracket further comprising a base frame portion having a periphery which is complementary with and removably attachable to a rear section of the chair, the base frame including a plurality of mounting locations, each of the chair accessories being arranged for attachment to a corresponding one or more of said mounting locations, in order to be positioned in an operative position on an exterior of the chair.

In still another of its aspects, the present invention provides a method of equipping a chair with accessories, comprising the steps of:
providing a chair with a frame supporting a seat portion and a back portion;
providing a mounting bracket assembly with a base frame portion having a periphery which is complementary with and removably attachable to a section of the chair;
providing a number of mounting locations on the mounting bracket assembly for removably mounting a number of chair accessories thereon;
installing the mounting bracket assembly on the chair; and
installing the accessories on the mounting bracket.

In yet another of its aspects, the present invention provides a conversion device for converting a recliner chair, comprising a base with one or more frame plate portions to engage a lower surface of the normally stationary recliner chair, and a plurality of mounting means for providing mounting locations for one or more peripheral articles for use with respect to the recliner chair.

In an embodiment, the accessories include one or more push bars positionable in selected ones of the second sleeve members for pushing the recliner.

In yet another of its aspects, the present invention provides a mounting bracket assembly for equipping a recliner with one or more accessories, comprising a pair of corner bracket units, each having a periphery which is complementary with and removably attachable to a corner region of the recliner, each corner bracket including bottom plate portion, a side plate portion and a rear base portion, wherein adjacent pairs of the plate portions are attached together along their edges, and a number of mounting formations on one or more of the plate members, each mounting formation being arranged to engage a complementary shaped mounting member on a recliner accessory article.

In still another of its aspects, the present invention provides a kit for converting a recliner chair, comprising a pair of corner bracket units, each having a periphery which is complementary with and removably attachable to a corner region of the recliner, each corner bracket including bottom plate portion, a side plate portion and a rear base portion, wherein adjacent pairs of the plate portions are attached together along their edges, and a number of mounting formations on one or more of the plate portions, the kit further comprising one or more of:

at least one push bar which is positionable in a corresponding mounting formation in one or more of the corner brackets so as to be adjacent a rear corner of the recliner chair, the push bar having a handle formation which is operatively positioned at an elevation within reach of a caregiver operator of the recliner;

a tray assembly having a mounting arm which is posiltionable one of said mounting formations, the tray assembly including an arm which is arranged to operatively position the tray adjacent the recliner;

one or more of a medication holder for securing a medication container; a holder for supporting a medical accessory and one or more bumper members for preventing damage to the recliner, each having at least one engaging means for engaging a corresponding mounting formation.

In an embodiment, the medication holder has a frame for securing the medication container, the frame being length extensible to accommodate varying lengths of medication containers.

In still another of its aspects, the present invention provides a mounting bracket for equipping an article with one or more accessories, comprising a base frame portion having a periphery which is complementary with and removably attachable to a section of the article, the base frame including a plurality of mounting locations for receiving the accessories in an operative position on an exterior of the article.

BRIEF DESCRIPTION OF THE DRAWINGS

Several preferred embodiments of the present invention will now be described, by way of example only, with reference to the appended drawings in which.

DESCRIPTION OF THE PREFERRED EMBODIMENTS

Figure 1:
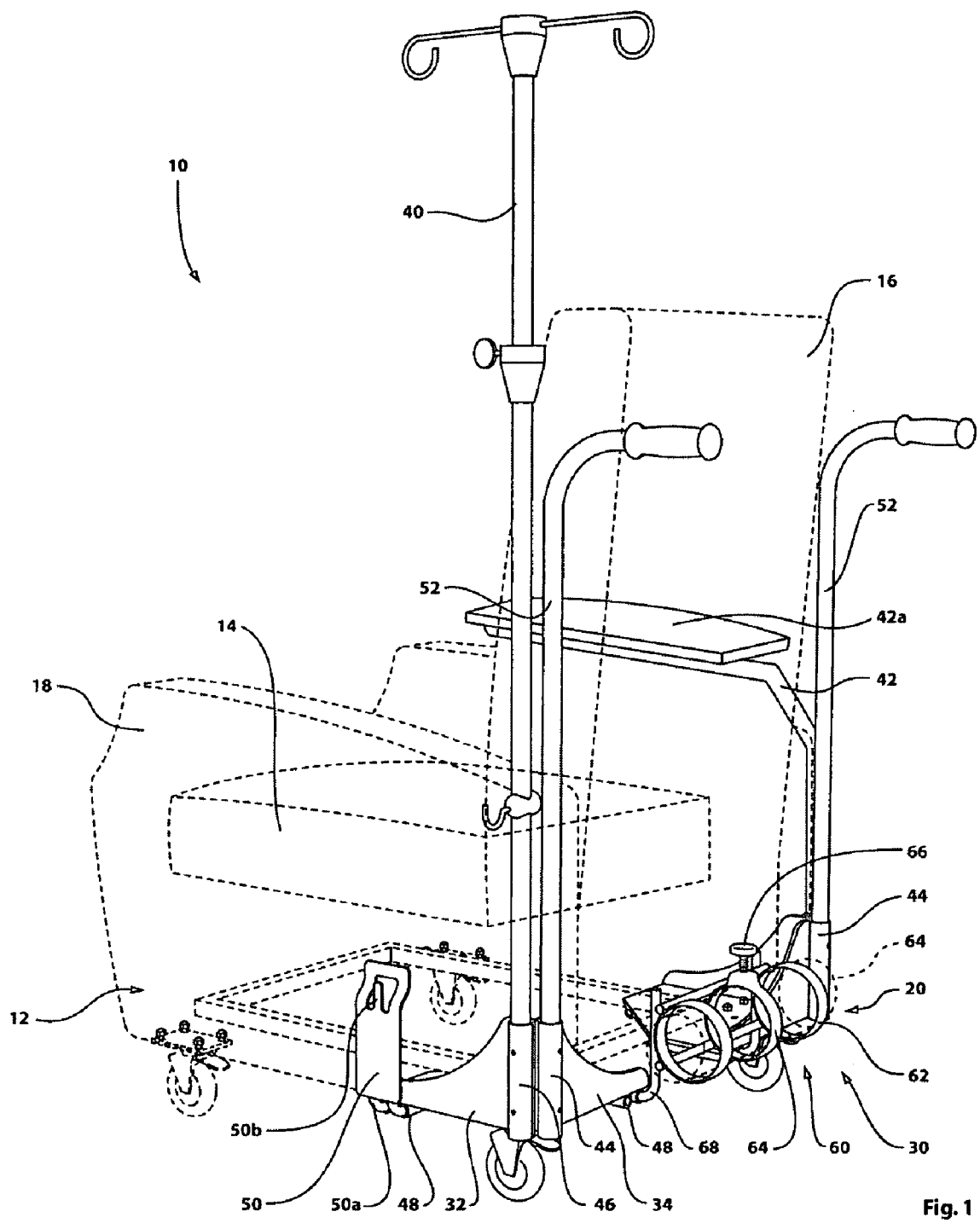
FIG. 1 is a perspective view of a recliner assembly.

Referring to the FIG. 1, there is provided a chair in the form of a recliner chair device 10 (referred hereinbelow also as a "recliner" and "recliner chair") having a recliner frame 12 supporting a seat portion 14, a back portion 16 and a pair of arm portions 18. An accessory portion 20 is attachable to the recliner frame 12 for equipping the recliner chair device with one or more accessories as will be described.

The accessory portion 20 includes an accessory base frame portion 30 attachable to the recliner frame 12. As will be described, the accessory base frame has a plurality of mounting locations and a plurality of recliner accessories, each of which is arranged for removable attachment to a corresponding one or more of said mounting locations. The accessories include one or more IV poles, one or more medication containers, one or more anchor or hook locations or a combination thereof. The accessories may also include one or more push bars for a caregiver to shift the location of the recliner. The accessories may also include a tray, for example having a support arm and on of the mounting locations includes a support arm receiving formation.

Figure 4:
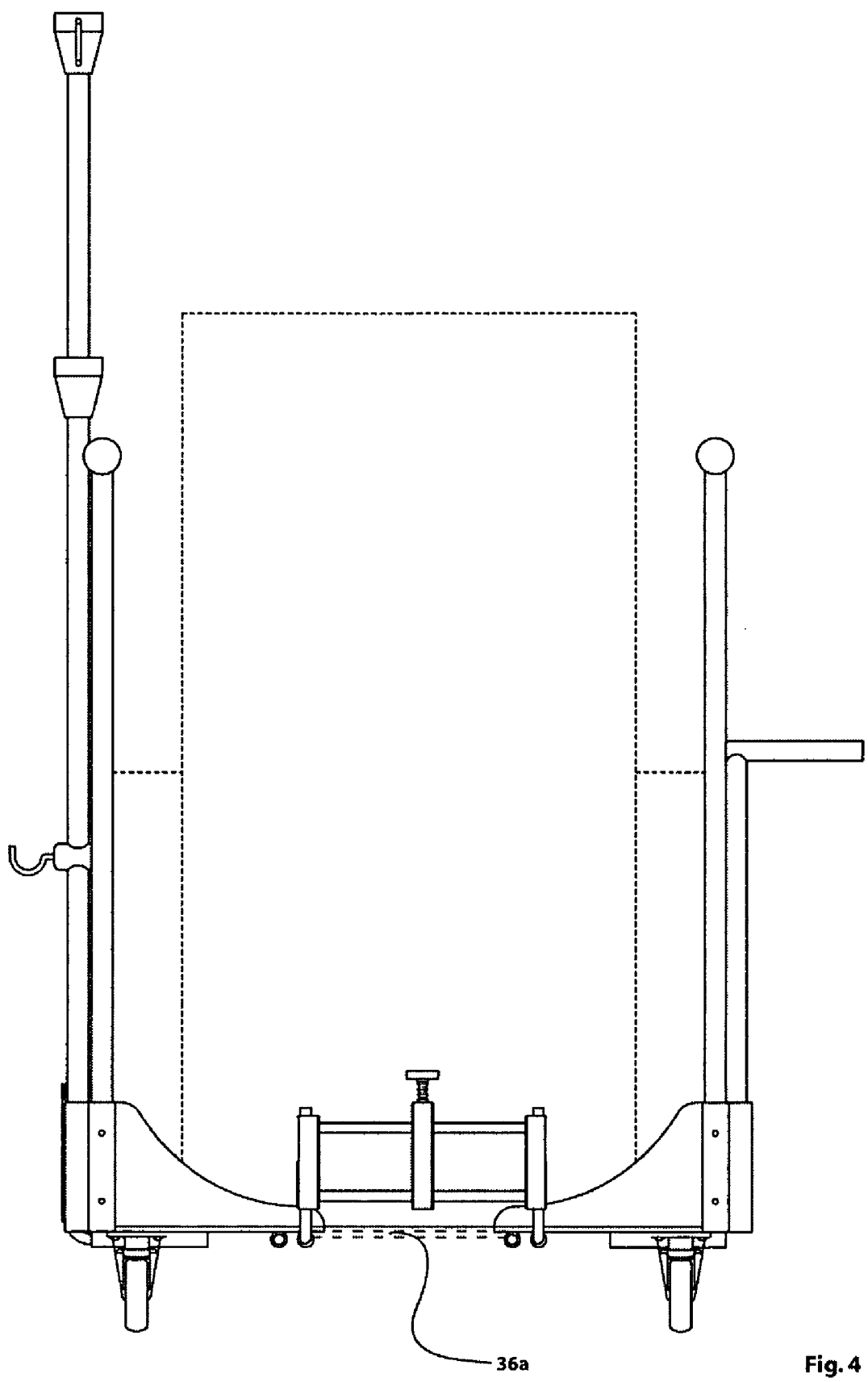
FIG. 4 is a rear view of the recliner assembly of FIG. 1.
Figure 5:
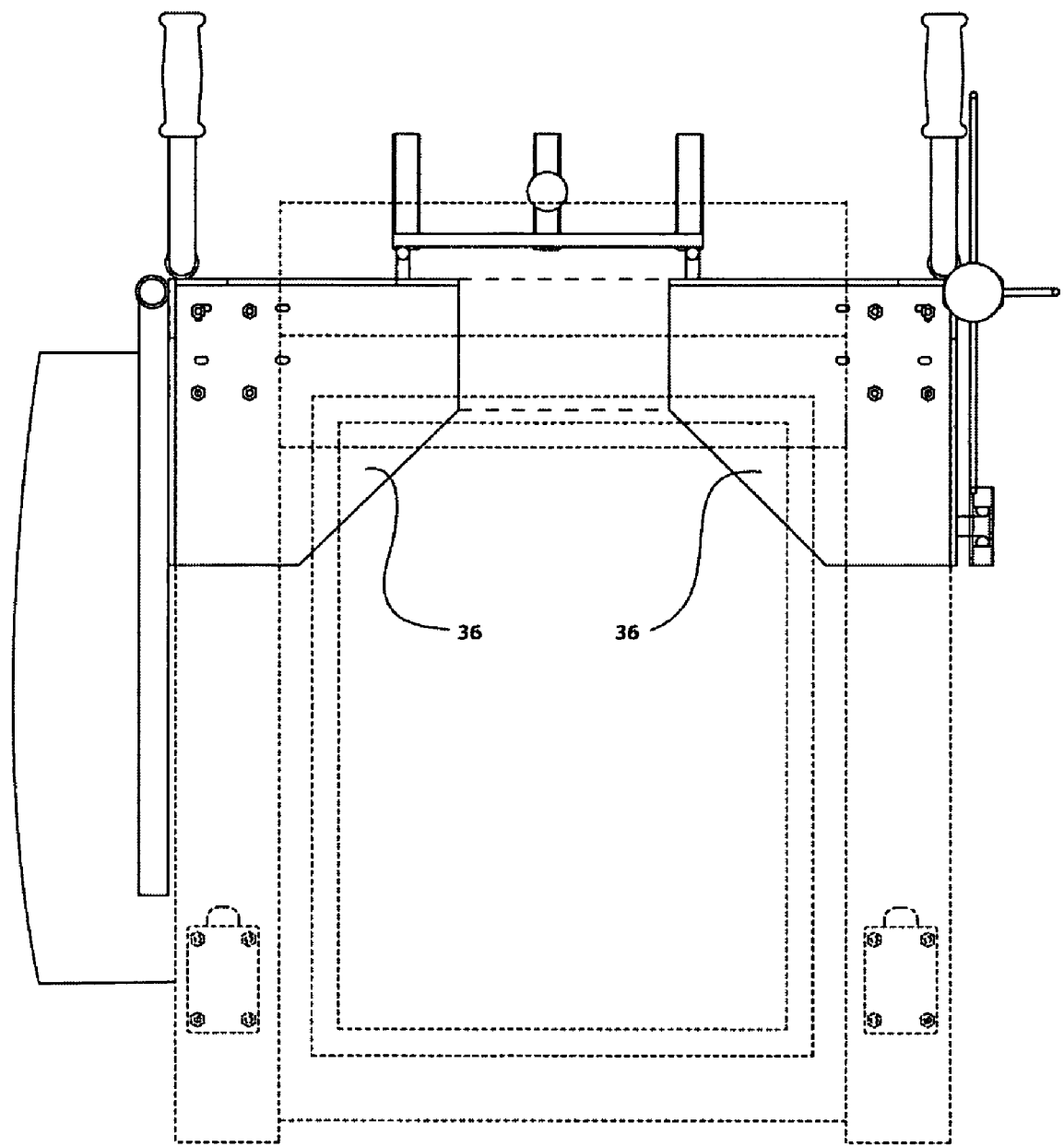
FIG. 5 is a plan view of a portion of the recliner assembly of FIG. 1.

The base frame portion 30 includes a pair of first plate portions 32 positioned for engaging opposite side regions of the recliner, a pair of second plate portions 34 positioned for engaging a back wall region of the recliner, and (as shown in FIG. 5) at least one third plate portion 36 for engaging a bottom region of the recliner. Each of the pair of first, second and third plate portions are located in a rear lower corner of the recliner frame 12 and, in each corner, the first, second and third plate portions are attached along their adjacent edges. If desired, one or more of the first, second or third plate portions from one side of the recliner may be joined to a coorepsonding opposite plate portion (i.e. on the opposite side of the recliner), such as by way of a spanning frame member shown in dashed lines at 36a joining the third plate portions together, as shown in FIG. 4. Alternatively, one or more of the first, second or third plate portions may form a continuous member with an opposing first, second or third plate portion. This is shown, for example, in FIG. 5 by the dashed lines illustrating a continuation of the third plate portions 36.

Figure 2:
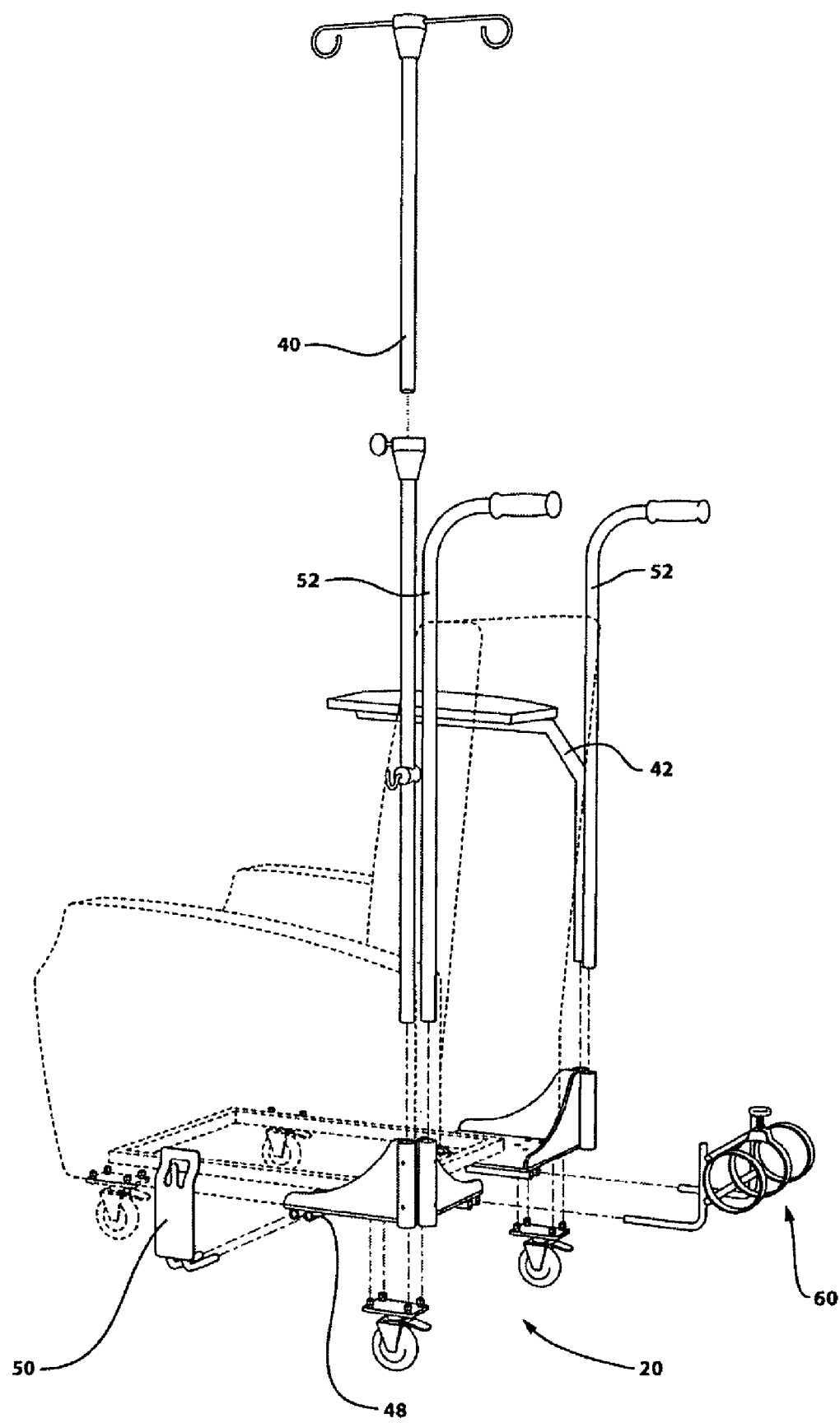
FIG. 2 is a perspective assembly view of the recliner assembly of FIG. 1.
Figure 3:
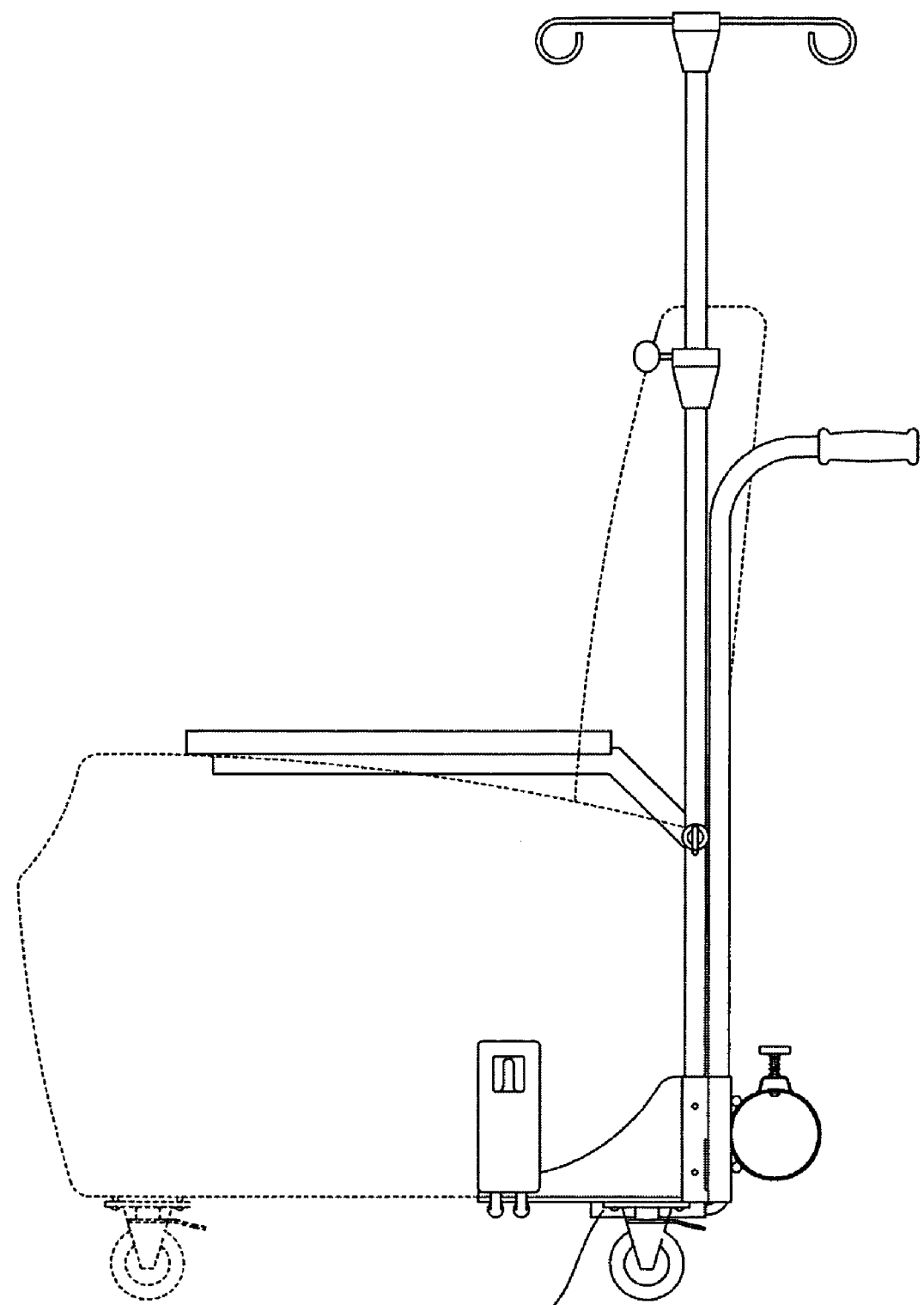
FIG. 3 is a side view of the recliner assembly of FIG. 1

Referring to FIG. 1, a number of the mounting locations are positioned on one or more of the first plate portions, one or more of the second plate portions, or one or more of the third plate portions, as desired. One or more of the locations includes a means for engaging an elongate member on an accessory, such as a lower portion of an extensible IV pole 40, or the lower portion of an arm 42 supporting a tray 42a. In both cases, the engaging means for supporting the IV pole 40 or the arm 42 include upright sleeve portions 44, 46 dimensioned to receive the corresponding elongate member therein. In addition, horizontally oriented sleeve portions are shown at 48 mounted on the third plate portions and facing both the rear and sides of the recliner (as shown in FIGS. 2 and 3).

FIG. 1 shows an accessory 50 having a pair of support arms 50a which are alignable with and removably inserted in the corresponding pair of sleeve portions 48. In this case, the accessory 50 includes a hook 50b. FIG. 1 also shows a pair of push handles 52 engaged with a corresponding sleeve portion 44.

FIG. 1 illustrates the second plate portions 34 spaced from one another and an engaging means 60 which is operable to carry a medication container. The engaging means 60 includes a number of frame rings 62 which are dimensioned to engage an outer surface of the medication container, such as an oxygen tank 64, with a central one of the frame rings 62 provided with a threaded fastener 66 to clamp against the container when loaded therein. In this case, the engaging means 60 also includes a pair of tubular engagement members 68 to engage the corresponding sleeve portions 48. FIG. 2 provides an exploded view of the accessory portion 20 and the accessories to be used therewith in this example, it being understood that other accessories may also be used which provide the same or similar mounting arrangement to engage the sleeve portions or other mounting formations on the accessory base frame portion 30.

Figure 6:
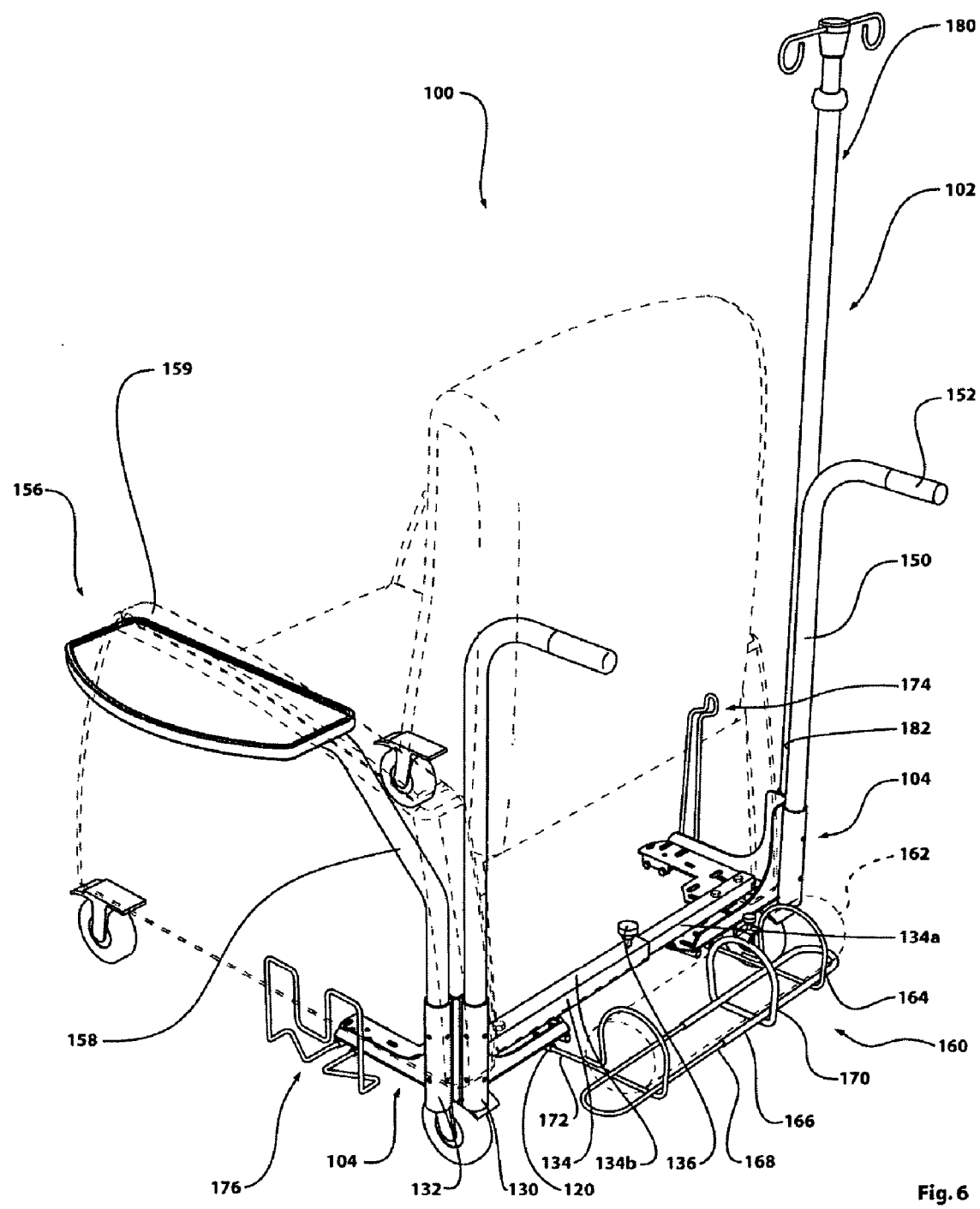
FIG. 6 is a perspective view of another recliner assembly.
Figure 9:
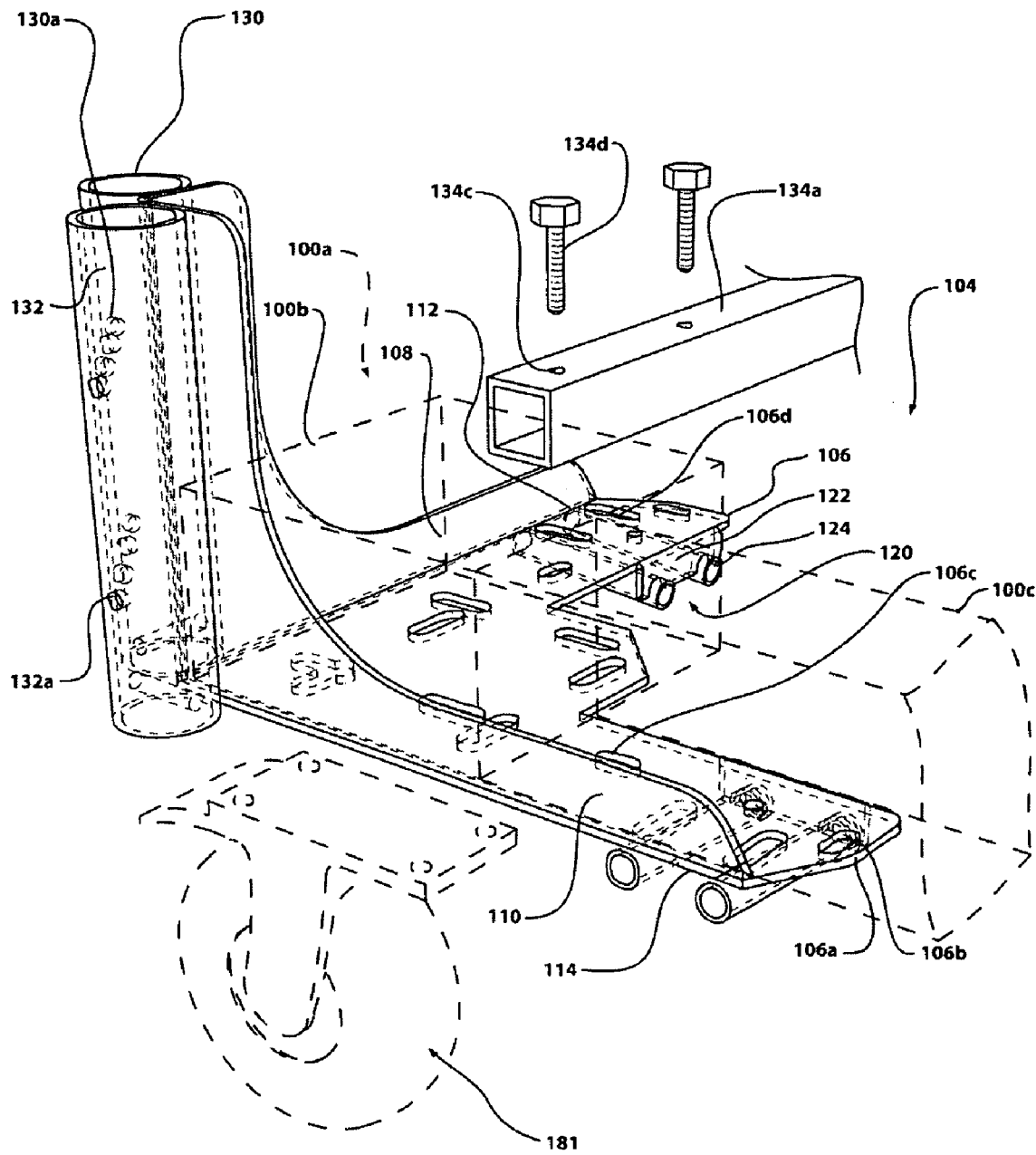
FIG. 9 is a perspective view of another a portion of the recliner assembly of FIG. 1.

Referring to FIG. 6, there is provided a recliner chair 100 shown in phantom and a conversion kit 102 for converting the recliner chair 100. In this case, the conversion kit 102 has a pair of corner brackets 104, each having a periphery which is complementary with and removably attachable to a corner region of the recliner chair 100. Referring to FIG. 9, each corner bracket 104 includes a bottom plate portion 106, a rear plate portion 108 and a side plate portion 110. The bracket is formed so that adjacent pairs of the plate portions are attached together along their mating edge regions 112, 114. A number of mounting formations, in the form of sleeve members 120, are provided on the plate portions 106.

In this case, the bottom plate portion 106 has a downwardly oriented flange 122 with a pair of locating recesses 124 formed therein to locate and position one end of each mounting formation 120 which, in this case, is a tube or sleeve member (itself welded or otherwise attached to the lower surface 106a of the bottom plate portion 106). The bottom plate has a number of passages to accommodate a number of fasteners in a range of positions so that the bracket can be used on a range of recliners. It will be understood that other passages may be provided as needed. Included are passages 106b and 106c for securing the bottom plate to the recliner. Referring to FIG. 6, extending between the corner brackets 104 is a support bar 134 having a pair of telescoping members 134a, 134b, each of which is mounted to a corresponding bottom plate 106. Referring to FIG. 9, the remote end portions of each telescoping member 134a, 134b has one or more passages 134c to receive a fastener 134d passing through the aligned passages 134c with passages 106d in the bottom plate. Referring to FIG. 6, the telescoping members 134a, 134b are also provided with a threaded clamp member 136 for fixing the length of the support bar 134 according to the width of the recliner. The support bar may be installed on the corner brackets 106 before they are installed on the recliner, if desired. A pair of vertical sleeve members 130, 132 is mounted to the rear plate portion 108 and the side plate portion 110 respectively. Each vertical sleeve member is respectively provided with a number of setting passages 130a, 132a to receive a locating pin on a complementary mounting arm for an accessory device, as will be described.

Figure 8:
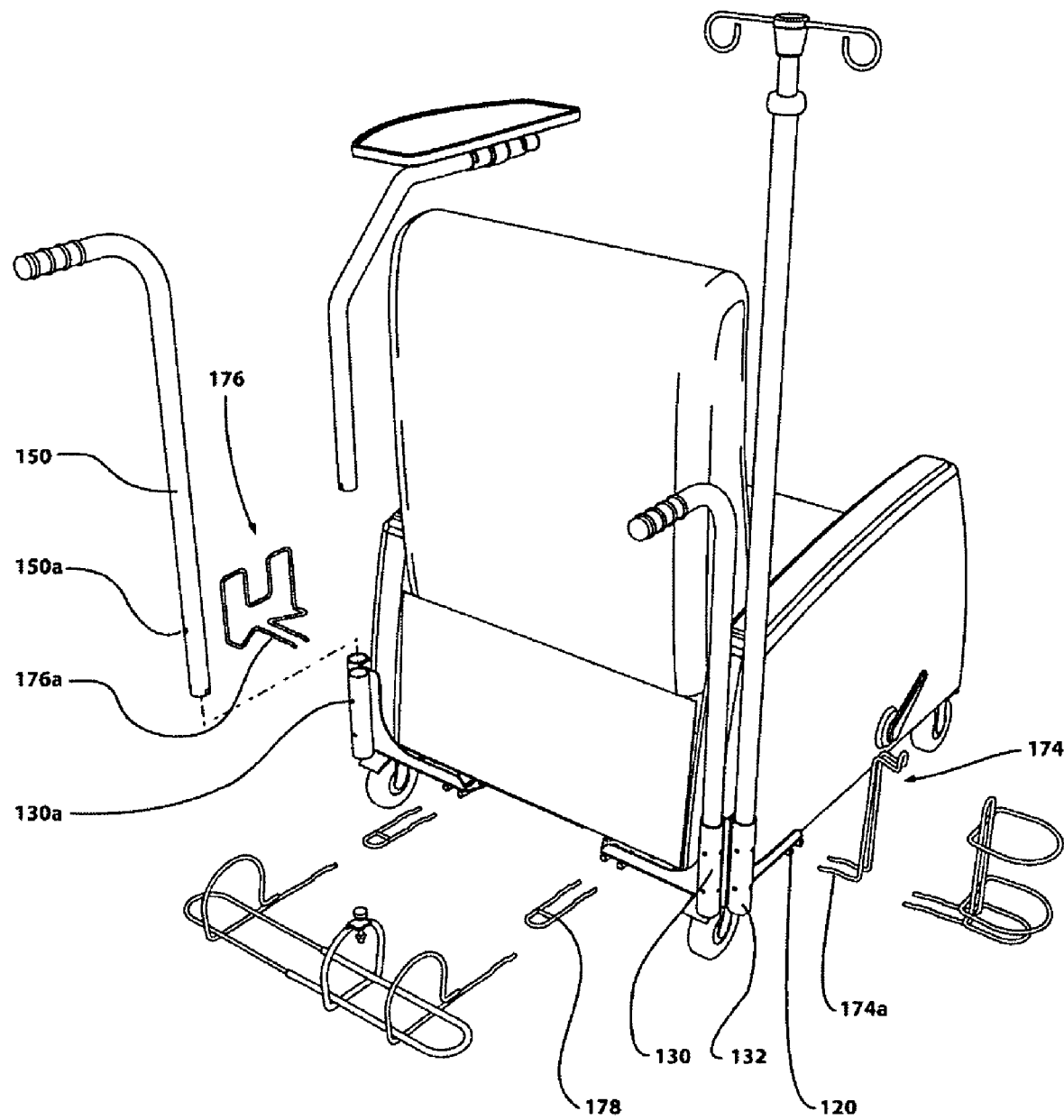
FIG. 8 is a rear perspective alternative assembly view of the recliner assembly of FIG. 5.
Figure 8A:
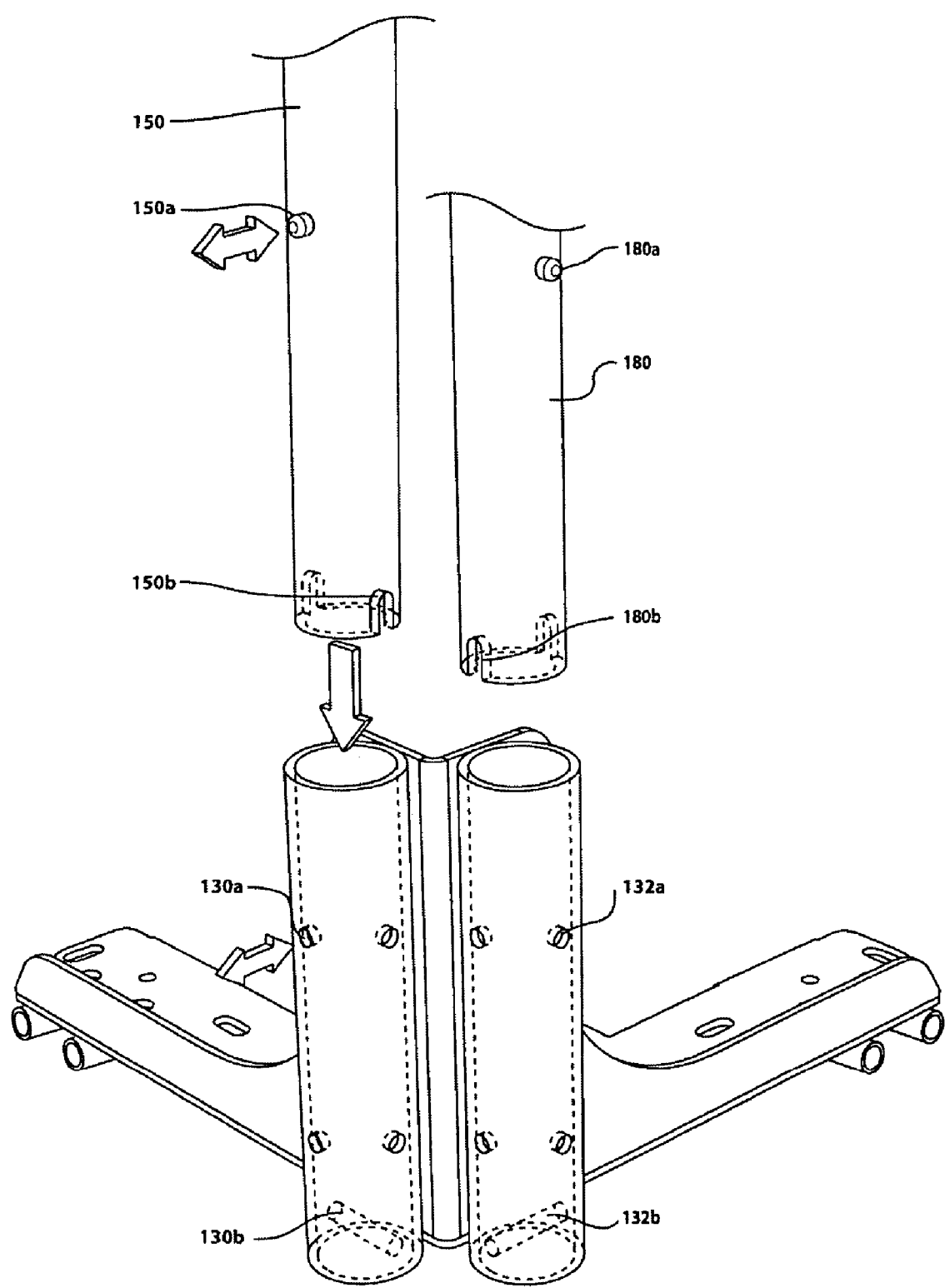
FIG. 8a is a perspective view of a portion of the assembly of FIG. 5.

Referring to FIG. 6, the kit 102 includes a pair of push bars 150, each of which is positionable in a corresponding mounting formation in one or more of the corner brackets 104 so as to be adjacent a rear corner of the recliner chair 100. In this case, the push bar has a handle formation 152 which is operatively positioned at an elevation within reach of a caregiver operator of the recliner chair 100. Referring to FIG. 8a, the push bar 150 is also provided with a releasable locking pin 150a which is received in the corresponding setting passage 130a. The push bar 150 is also provided with a pair of diametrically opposed recesses 150b which are dimensioned to engage a corresponding anchor pin 130b located in the sleeve portion 130, to inhibit rotation of the push bar when in an operative position therewith.

Figure 7:
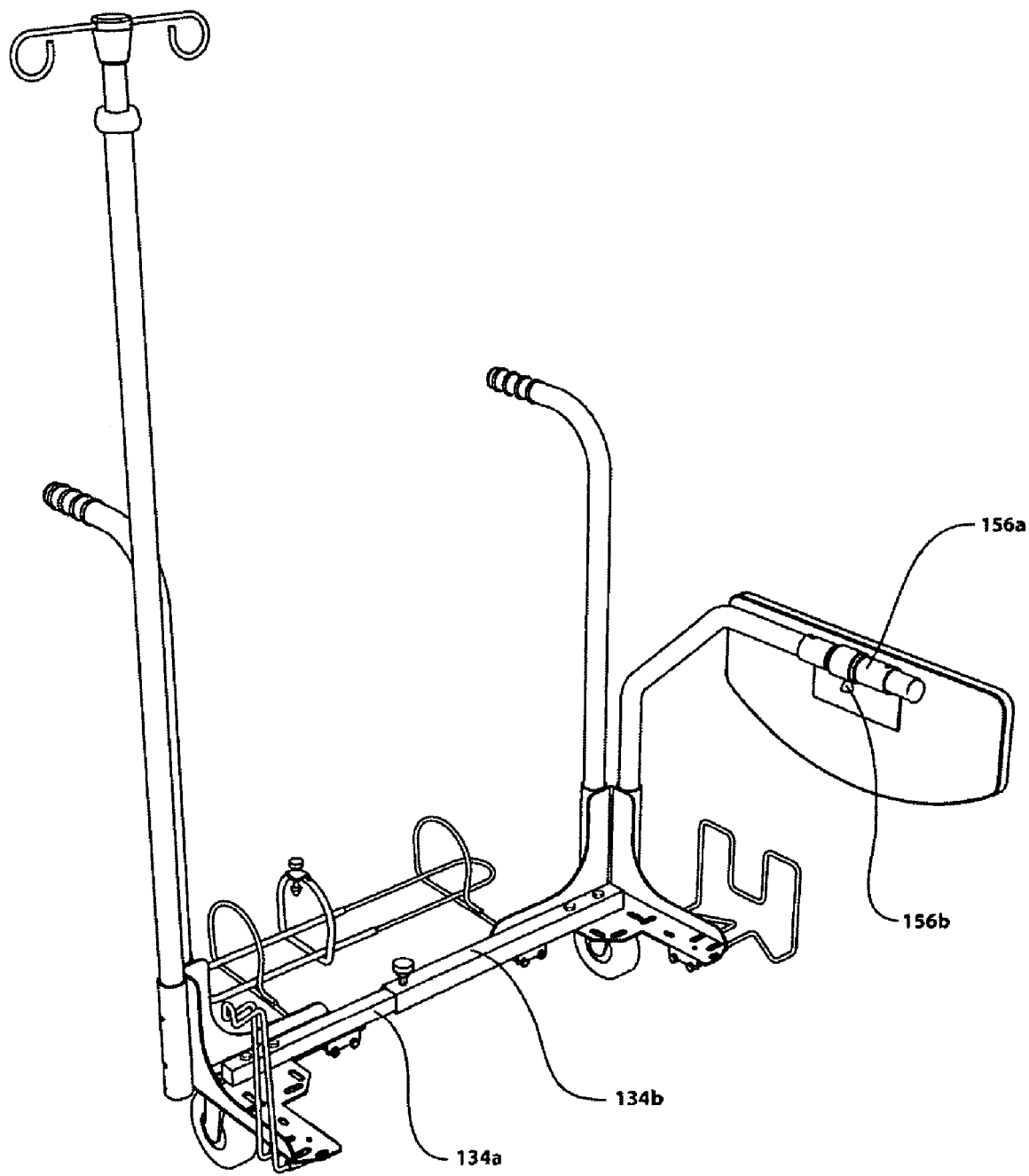
FIG. 7 is a perspective view of a portion of the recliner assembly of FIG. 5.

Referring to FIG. 6, the kit also includes a tray assembly 156 having a mounting arm 158 which is positionable on one of the mounting formations. In this case, the arm 158 is arranged to operatively position the tray adjacent the recliner chair 100, for example beside an upper region of the arm 159. Referring to FIG. 7, the tray is mounted on a sleeve 156a, itself on slidable relative to mounting arm 158. In this manner, the tray is movable between a storage position shown in FIG. 7 and an operable position in FIG. 6 and secured therein by releasable pin 156b, through holes appropriately located in the arm 158.

Referring to FIG. 6, the kit also includes a medication holder, as shown at 160, for securing a medication container, such as a gas canister 162, such as that contining oxygen. The medication holder has a length extensible frame 164 for accommodating different length canisters. To this end, the frame has a pair of U-shaped frame members 166, 168 whose free ends are in telescoping relationship and a number of ring members 170, two of which are mounted on frame member 166 and one of which is mounted on frame member 168.

Two of the ring members 170 are also provided with free end portions 172 which engage a corresponding sleeve member 120. Also provided is a number of supporting accessories, such as a hook member 174 for supporting such things as a urinary bag and a frame member 176 for supporting magazines and the like. As shown in FIG. 8, the hook member 174 and the frame member 176 have mounting fingers 174a, 176a respectively to be received in corresponding sleeve members 120. If desired, the hook member 174 and frame member 176 may fabricated with the spacing between the mounting fingers 174a, 176a being wider than the spacing of the sleeve members 120 when the mounting fingers are installed in the corresponding sleeve members 120 to give the mounting fingers a laterally outward bias to aid in keeping the hook members 174 and frame members 176 in place. Other means may also be used to maintain the one or more accessories in their mounted position, such as releasable or removable locking pins or the like. In addition, the accessories may include such things as bumper members 178 as shown in FIG. 8 to protect the chair from contact with walls, other furniture and the like. Of course, the vertical sleeve members 130, 132 and the horizontal sleeve members 120 may be used to mount other accessories on the recliner as desired such as computer monitors, leg and arm supports, brackets and the like. While the sleeve members 120 are disclosed in this particular embodiment as horizontal and the sleeve members 130, 132 are described as vertical, they may of course be provided in other orientations or, for that matter may be adjustable as may be needed or desirable when mounting accessories on the recliner, either those mentioned herein or those not listed herein.

Referring to FIG. 6, a height adjustable IV stand 180 is also provided with a mounting arm 182 which is similarly dimensioned to that of mounting arm 158 so that the former may also be positioned in a corresponding sleeve member 132. Like the push bar 150, the IV stand 180 is has a releasable locating pin 180a aligned with and lodged in the corresponding setting passage 132a in the sleeve portion. 132 and a pair of diametrically opposed recesses 180b which are dimensioned to engage a corresponding anchor pin 132b located in the sleeve portion 132, to inhibit rotation of the IV when in an operative position therewith.

Both the accessory portion 20 used on the recliner 10 and the kit 102 described for use on the recliner 100 enable a normally stationary recliner or other chair to be retrofitted in a manner in which it can be converted relatively easily to a mobile recliner by providing the needed rolling undercarriage as well as the push bars needed for medical personnel to push the now mobile recliner. However, it will also be understood that the accessory portion 20 and the kit 102 may also be used on recliners that are mobile, but lack the accessory mounting location for one or more of the accessories provided in the accessory portion 20 and/or the kit 102. While the accessory portion 20 and the kit 102 are particularly useful for retrofit purposes, it will also be understood that the accessory portion and kit 102, or portions thereof, may be used in the initial manufacture of a recliner to make the recliner capable of being used with a wider range of accessories.

The retrofitting of a recliner will now be described with reference to the kit 102. If the recliner 100 is already provided with casters, the caster assembly is removed from each rear corner region of the recliner 100. Referring to FIG. 9, the corner brackets 104 are then installed in each corner region by one or more threaded fasteners passing through one or more of the passages provided in the bottom plate portion, for example as provided at 106b and 106c to secure each corner bracket into a frame portion of the recliner 100, shown schematically at 100a. In this case, the frame portion 100a has a relatively wide portion 100b which is located in the corner and a relatively narrow span 100c extending in a forward direction from the corner along a side periphery of the recliner 100. It will be understood that the relatively wide portion is dimensioned, among other reasons, to provide a suitably dimensioned seat for the frame on the caster assembly shown at 181. It will be understood that the passages 106b and 106c are provided on both wings of the bottom plate 106 to allow the same corner bracket to be used in either rear corner of the recliner.

With each corner bracket secured to the frame portion of the recliner 100, the support bar 134 may be installed as described above (if not already in place) followed by the installation of the accessories. For instance, the push bars 150 may each be aligned with a corresponding sleeve member 130 and the releasable locating pin 150a aligned with and lodged in the corresponding setting passage 130a depending on the position desired for the push bar 152. It follows that the number of setting passages 130a may be increased as desired to increase the number of available positions for the push bars 150.

The tray assembly 156 and or IV stand 180 may then be installed in a corresponding sleeve member 132. Next the medication holder 160 is installed by adjusting the spacing of the two free end portions 172 of the ring portions 170 in order to match the spacing between the corresponding sleeve members 120. The medication holder 160 is then installed by passing the free end portions 172 through the sleeve members 120. Next, the urinary hook 174 and frame member 176 may be installed by aligning their mounting figures 174a, 176a with the corresponding sleeve members 120 and inserting the former in the latter.

While the present invention has been described for what are presently considered the preferred embodiments, the invention is not so limited. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

While the accessories herein are described as being removably installed on the recliner, it will be understood that one or more of the accessories may also be rendered permanently attached to the corresponding mounting location by welding or the like. While the brackets shown here are attachable to the rear section of the recliner, they may, alternatively, be mounted in another section of the recliner, such as, for example, the front section. Furthermore, a bracket may be attachable to each corner of the recliner, if need be. In addition, the bracket assembly and accessories and other features described herein are applicable to other chairs which may or may not be mobile and may or may not recline. In addition, the bracket assembly and accessories and other features described herein are applicable to other articles, be they used in a medical environment, a human transport or other environment, and which are receptive to the bracket assembly or other features as described herein.

The invention claimed is:

1. An accessory mounting device for a recliner chair having a chair frame, the accessory mounting device comprising:
    a base frame portion for attachment to the chair frame, the base frame portion comprising:
        a pair of first plate portions for engaging opposite side regions of the chair frame,
        at least one second plate portion for engaging a rear region of the chair frame, and
        at least one third plate portion for engaging a bottom region of the chair frame;
    a plurality of upright sleeve portions provided on the base portion, wherein at least one of the plurality of upright sleeve portions is provided on each of the pair of first plate portions, and wherein at least one of the plurality of upright sleeve portions is provided on the at least one second plate portion;
    a plurality of horizontal sleeve portions provided on the base portion, wherein at least one of the plurality of horizontal sleeve portions is provided on the at least one third plate portion; and
    at least one accessory selected from the group consisting of:
        a push handle including an elongate member adapted to be removably received within one of the plurality of upright sleeve portions,
        an IV pole including an elongate member adapted to be removably received within one of the plurality of upright sleeve portions,
        a tray assembly having a mounting arm including an elongate member adapted to be removably received within one of the plurality of upright sleeve portions,
        a urinary bag holder including a mounting finger adapted to be removably received within one of the plurality of horizontal sleeve portions,
        a document holder including a mounting finger adapted to be removably received within one of the plurality of horizontal sleeve portions, and
        a gas cylinder holder including a mounting finger adapted to be removably received within one of the plurality of horizontal sleeve portions.

2. The accessory mounting device according to claim 1 comprising a pair of second plate portions and a pair of third plate portions, wherein one of the pair of first plate portions, one of the pair of second plate portions and one of the pair of third plate portions are joined together to form a left corner formation for engaging a lower left rear corner region of the chair frame, and the other of the pair of first plate portions, the other the pair of second plate portions and the other of the pair of third plate portions are joined together to form a right corner formation for engaging a lower right rear corner region of the recliner frame.

3. The accessory mounting device according to claim 2 further comprising a pair of rear casters, wherein one of the pair of rear casters is adapted for engagement with an underside of the third plate portion of the left corner formation and the other of the pair of rear casters is adapted for engagement with an underside of the third plate portion of the right corner formation.

4. A recliner accessories mounting device comprising:
a base frame portion for engagement with a chair frame of a recliner chair, the base frame portion comprising
a left corner formation for engagement with a lower left rear corner region of the chair frame, the left corner formation comprising
a left bottom portion for engagement with a bottom region of the chair frame,
a left side portion for engagement with a left side region the chair frame, and
a left rear portion for engagement with a rear region of the chair frame, and
a right corner formation for engagement with a lower right rear corner region of the chair frame, the right corner formation comprising
a right bottom portion for engagement with the bottom region of the chair frame,
a right side portion for engagement with a right side region the chair frame, and
a right rear portion for engagement with the rear region of the chair frame,
a plurality of upright sleeve portions provided on the base frame portion, wherein at least one of the plurality of upright sleeve portions is provided on the left side portion of the left corner formation, wherein at least one of the plurality of upright sleeve portions is provided on the left rear portion of the left corner formation, wherein at least one of the plurality of upright sleeve portions is provided on the right side portion of the right corner formation, wherein at least one of the plurality of upright sleeve portions is provided on the right rear portion of the right corner formation, and wherein each of the plurality of upright sleeve portions is adapted to removably receive a recliner accessory elongate member; and
a plurality of horizontal sleeve portions provided on the base portion, wherein at least one of the plurality of horizontal sleeve portions is provided on the left bottom portion of the left corner formation, wherein at least one of the plurality of horizontal sleeve portions is provided on the right bottom portion of the right corner formation, and wherein each of the plurality of horizontal sleeve portions is adapted to removably receive a recliner accessory mounting finger.

5. The device according to claim 4 further comprising an undercarriage assembly comprising a left rear caster wheel for engagement with the left bottom portion of the left corner formation, a right rear caster wheel for engagement with the right bottom portion of the right corner formation, a left front caster wheel for attachment to a left front corner of the bottom region of the chair frame, and a right front caster wheel for attachment to a right front corner of the bottom region of the chair frame.

6. The device according to claim 4 further comprising a pair of push handles, wherein each push handle includes an elongate member adapted to be removably received within one of the plurality of upright sleeve portions.

7. The device according to claim 6 wherein one of the pair of push handles is adapted to be removably received in the upright sleeve portion provided on the left rear portion of the left corner formation and the other one of the pair of push handles is adapted to be removably received in the upright sleeve portion provided on the right rear portion of the right corner formation.

8. The device according to claim 7 wherein when the pair of push handles are received in the upright sleeve portions, the pair of push handles are spaced apart sufficiently to permit a back portion of the recliner chair to be reclined therebetween.

9. The device according to claim 7 further comprising an IV pole, wherein the IV pole includes an elongate member adapted to be removably received within one of the plurality of upright sleeve portions provided on either the left side portion of the left corner formation or the right side portion of the right corner formation.

10. The device according to claim 7 further comprising a tray assembly, wherein the tray assembly includes an elongate member adapted to be removably received within one of the plurality of upright sleeve portions provided on either the left side portion of the left corner formation or the right side portion of the right corner formation.

11. The device according to claim 4 wherein each of the plurality of upright sleeve portions is provided with a setting passage for receiving a releasable locating pin extending from the recliner accessory elongate member.

12. The device according to claim 11 wherein each of the plurality of upright sleeve portions is provided with an anchor pin for engaging a pair of diametrically opposed recesses formed the recliner accessory elongate member to inhibit rotation of the recliner accessory elongate member when received within the upright sleeve portion.

13. The device according to claim 4 further comprising a urinary bag holder, wherein the urinary bag holder includes a pair of mounting fingers, each of which is adapted to be removably received within one of the plurality of horizontal sleeve portions.

14. The device according to claim 4 further comprising a document holder, wherein the document holder includes a pair of mounting fingers, each of which is adapted to be removably received within one of the plurality of horizontal sleeve portions.

15. The device according to claim 4 further comprising a gas cylinder holder, wherein the gas cylinder holder includes a pair of mounting fingers, each of which is adapted to be removably received within one of the plurality of horizontal sleeve portions.

16. The device according to claim 4 further comprising a pair of bumper members, wherein each of the pair of bumper members includes a pair of mounting fingers, each of which is adapted to be removably received within one of the plurality of horizontal sleeve portions.

17. The device according to claim 4 further comprising a hook member for supporting a urinary bag, wherein the hook member includes a pair of mounting fingers, each of which is adapted to be removably received within one of the plurality of horizontal sleeve portions.

18. The device according to claim 4 wherein the left bottom portion, the left side portion and the left rear portion of the left corner formation are attached together along their edges, and wherein the right bottom portion, the right side portion and the right rear portion of the right corner formation are attached together along their edges.

19. The device according to claim 4 wherein the left bottom portion of the left corner formation and the right bottom portion of the right corner formation are joined together by means of a spanning bottom portion frame member and/or the left rear portion of the left corner formation and the right rear portion of the right corner formation are joined together by means of a spanning rear portion frame member.

20. In combination, a recliner chair and a recliner accessories mounting device, wherein the recliner chair comprises a chair frame supporting a seat portion, a reclinable back portion and a pair of arm portions, and wherein the the recliner accessories mounting device comprises:
- a base frame portion base frame portion comprising
  - a left corner formation engaged with a lower left rear corner region of the chair frame, the left corner formation comprising
    - a left bottom portion engaged with a bottom region of the chair frame,
    - a left side portion engaged with a left side region the chair frame, and
    - a left rear portion engaged with a rear region of the chair frame, and
  - a right corner formation engaged with a lower right rear corner region of the chair frame, the right corner formation comprising
    - a right bottom portion engaged with the bottom region of the chair frame,
    - a right side portion engaged with a right side region the chair frame, and
    - a right rear portion engaged with the rear region of the chair frame,
- a plurality of upright sleeve portions provided on the base frame portion, wherein at least one of the plurality of upright sleeve portions is provided on the left side portion of the left corner formation, wherein at least one of the plurality of upright sleeve portions is provided on the left rear portion of the left corner formation, wherein at least one of the plurality of upright sleeve portions is provided on the right side portion of the right corner formation, wherein at least one of the plurality of upright sleeve portions is provided on the right rear portion of the right corner formation;
- a plurality of horizontal sleeve portions provided on the base portion, wherein at least one of the plurality of horizontal sleeve portions is provided on the left bottom portion of the left corner formation, wherein at least one of the plurality of horizontal sleeve portions is provided on the right bottom portion of the right corner formation;
- a pair of push handles, wherein one of the pair of push handles is removably received in the upright sleeve portion provided on the left rear portion of the left corner formation and the other one of the pair of push handles is removably received in the upright sleeve portion provided on the right rear portion of the right corner formation, and wherein said pair of push handles are spaced apart sufficiently to permit the back portion of the recliner chair to be reclined therebetween;
- an undercarriage assembly comprising a left rear caster wheel engaged with the left bottom portion of the left corner formation, a right rear caster wheel engaged with the right bottom portion of the right corner formation, a left front caster wheel attached to a left front corner of the bottom region of the chair frame, and a right front caster wheel attached to a right front corner of the bottom region of the chair frame; and
- one or more recliner accessories selected from the group consisting of:
  - an IV pole including an elongate member adapted to be removably received within one of the plurality of upright sleeve portions,
  - a tray assembly having a mounting arm including an elongate member adapted to be removably received within one of the plurality of upright sleeve portions,
  - a urinary bag holder including a mounting finger adapted to be removably received within one of the plurality of horizontal sleeve portions,
  - a document holder including a mounting finger adapted to be removably received within one of the plurality of horizontal sleeve portions, and
  - a gas cylinder holder including a mounting finger adapted to be removably received within one of the plurality of horizontal sleeve portions.

\* \* \* \* \*